United States Patent [19]

Ayres et al.

[11] Patent Number: 5,260,061
[45] Date of Patent: * Nov. 9, 1993

[54] PROPIONIBACTERIA METABOLITES INHIBIT SPOILAGE YEAST IN FOODS

[75] Inventors: James W. Ayres; William E. Sandine, both of Corvallis; George H. Weber, Beaverton, all of Oreg.

[73] Assignee: The State of Oregon Acting by and through the State Board of Higher Education on Behalf of Oregon State University, Eugene, Oreg.

[*] Notice: The portion of the term of this patent subsequent to Mar. 17, 2009 has been disclaimed.

[21] Appl. No.: 852,292

[22] Filed: Mar. 16, 1992

Related U.S. Application Data

[63] Continuation-in-part of Ser. No. 192,231, May 9, 1988, Pat. No. 5,096,718, which is a continuation-in-part of Ser. No. 753,563, Jul. 10, 1985, abandoned, which is a continuation-in-part of Ser. No. 419,559, Sep. 17, 1982, abandoned.

[51] Int. Cl.$^5$ .................. A23C 3/08; A23C 13/16; A23C 19/11; A23L 3/00
[52] U.S. Cl. ..................... 424/115; 426/34; 426/36; 426/43; 426/51; 426/52; 426/61; 426/321; 426/330.2; 426/330.3; 426/330.5; 426/334; 426/335
[58] Field of Search ............ 424/115; 426/34, 36, 43, 51, 52, 61, 321, 330.2, 330.3, 330.5, 334, 335

[56] References Cited

U.S. PATENT DOCUMENTS

| | | | |
|---|---|---|---|
| 1,449,959 | 6/1923 | Sherman et al. | 435/42 |
| 1,470,885 | 10/1923 | Sherman et al. | 435/141 |
| 1,910,130 | 5/1933 | Sherman | 435/141 |
| 1,937,672 | 12/1933 | Sherman | 435/141 |
| 2,154,499 | 4/1939 | Hoffman et al. | 433/219 |
| 2,465,905 | 3/1949 | Meade et al. | 426/41 |
| 3,404,987 | 10/1968 | Kooistra et al. | 426/9 |
| 3,681,091 | 8/1972 | Kohl et al. | 426/532 |
| 3,779,796 | 12/1973 | Vena et al. | 562/606 |
| 3,812,269 | 5/1974 | Mueller et al. | 426/97 |
| 3,846,567 | 11/1974 | Matyas et al. | 426/289 |
| 3,895,116 | 7/1975 | Herting et al. | 514/557 |
| 3,928,620 | 12/1975 | Courtade et al. | 514/557 |
| 4,199,606 | 4/1980 | Bland | 426/331 |
| 4,308,293 | 12/1981 | Tribble et al. | 426/532 |
| 4,497,833 | 2/1985 | Anderson | 426/41 |
| 4,728,516 | 3/1988 | Baudreaux et al. | 435/885 |
| 4,806,368 | 2/1989 | Reddy | 426/61 |
| 4,981,705 | 1/1991 | Tomes | 426/807 |
| 5,096,718 | 3/1992 | Ayres et al. | 426/9 |

FOREIGN PATENT DOCUMENTS

| | | |
|---|---|---|
| 618210 | 4/1961 | Canada . |
| 1061632 | 9/1979 | Canada . |
| 1218894 | 2/1992 | Canada . |
| 2048977 | 2/1992 | Canada . |
| 0095268 | 11/1983 | European Pat. Off. . |
| 0096477 | 12/1983 | European Pat. Off. . |
| 233566 | 8/1987 | European Pat. Off. . |
| 2190365 | 1/1974 | France . |
| 71-2942 | 1/1972 | South Africa . |
| 1321702 | 6/1973 | United Kingdom . |
| 1420237 | 1/1976 | United Kingdom . |
| 2060346 | 5/1981 | United Kingdom . |

OTHER PUBLICATIONS

Lee et al., *Can J. Microbiol.*, vol. 16, pp. 1231–1242 (1970).

Wolford et al., *Food Ind*, vol. 17, pp. 622–625, 726–734 (1945).

(List continued on next page.)

*Primary Examiner*—Glennon H. Hollrah
*Assistant Examiner*—Scott C. Rand
*Attorney, Agent, or Firm*—Klarquist, Sparkman, Campbell, Leigh and Whinston

[57] ABSTRACT

A metabolite material of propionibacteria is added to a food product to inhibit the growth of yeast. The metabolite material is produced by growing propionibacteria cells in a liquid growth medium to produce a mixture containing the metabolite material. The mixture can be concentrated and added to a food product as a concentrated liquid or powder. The metabolite material added to a food product may contain viable cells of propionibacteria.

4 Claims, No Drawings

OTHER PUBLICATIONS

Bhunia et al., "Direct Detection of an Antimicrobial Peptide of *Pediococcus aidilactici* in Sodium Dodecyl Sulfate-Polyacrylamide Gel Electrophoresis," *J. Indust. Microbiol.* 2:1b–4b (1987).

Chung et al., "Growth of Salmonella at Low pH," *J. Food Sci.*, 35:326 (1970).

*Compendium of Methods for the Microbiological Examination of Foods*, "ASLA Agar for Propionibacteria," pp. 65 et seq. (1976).

*The Condensed Chemical Dictionary*, 10th ed., UNR, N.Y. p. 862 (1981).

*Handbook of Food Additives*, CRC Press, 2nd ed., 137–184 (1972).

Hettinga et al., "Pouch Method for Isolating and Enumerating Propionibacteria," *J. Dairy Sci.* 51:1707–1709 (1968).

Hettinga et al., "The Propionic-Acid Bacteria—A Review," *J. Milk Food Technol.* 35:295–301, 358–372, 436–447 (1972).

Ingle, "Some Preliminary Observations on the Effectiveness of Propionates as Mold Inhibitors on Dairy Products," *J. Dairy Sci.* 23:509 (1940).

Isshiki et al., "Preservatives and Artificial Sweeteners," *J. Assoc. Off. Anal. Chm.* 64:280–281 (1981).

Jackel et al., "A New Dried Dairy Culture Ingredient for Bakers," *The Bakers Digest* 6:38–39 (1975).

Jennes et al., *Principles of Dairy Chemistry*, Chapman & Hall, N.Y. 370–375 (1959).

Johnston et al., "Incidence of Salmonella in Fresh Pork Sausage in 1979 Compared with 1969," *J. Food Sci.* 47:1369–1371 (1982).

Kishishita et al., "New Medium for Isolating Propionibacteria and Its Application to Assay of Normal Flora of Human Facial Skin," *App. & Env. Microbiol.* 10:1100–1105 (1980).

Kosikowski, *Cheese and Fermented Milk Foods*, pub'd by author, Ithaca, N.Y. 12, 15,47–49, 235–330 (1966).

Kriek et al., "Toxicity of *Penicillium Italicum* to Laboratory Animals," *Fd. Cosmet. Toxicol.* 19:311–315 (1981).

Langsrud et al., "Flavor Development and Microbiology of Swiss Cheese—A Review: I. Milk Quality and Treatments," *J. Milk Food Technol.* 36:487–490 (1973).

Langsrud et al., "Flavor Development and Microbiology of Swiss Cheese—A Review: II. Starters, Manufacturing Processes and Procedures," *J. Milk Food Technol.* 36:531–542 (1973).

Langsrud et al., "Flavor Developement and Microbiology of Swiss Cheese—A Review: III. Ripening and Flavor Production," *J. Milk Food Technol.* 36:593–609 (1973).

Langsrud et al., "Flavor Development and Microbiology of Swiss Cheese—A Review: IV. Defects," *J. Milk Food Technol.* 37:26–41 (1974).

Lindsay et al., "Identification of Volatile Flavor Components of Butter Culture," *Jour. Dairy Sci.* 43:1566–1574 (1965).

Macy, "Mold Inhibitors for Food Products," *Assn Food & Drug Officials, Quart. Bul.* 6:9–12 (1942).

Majchrzak et al., "Studies on Bread Preservation and Enrichment in Vitamins B12 & Calcium, Part I," *Technol. Riono-Spozyw* (*Zeuz. Nauk Szh. Gl. Gospod. Wiejsk, Akad. Roln. Warszawie*) 12:23–35 (1977).

Malik et al., "An Evaluation of the Taxonomy of Propionibacterium," *Canadian J. Microbiol.* 14:1185–1191 (1968).

Marsili et al., "High Performance Liquid Chromatographic Determination of Organic Acids in Dairy Products," *J. Food Sci.* 46:52–57 (1981).

*The Merck Index*, 9th ed., p. 7614 (1976).

Miller, "Mold Growth on Cheddar Cheese and Its Control," *Proceedings, Institute of Food Technol.* 1:153–158 (1940).

Nieuwenhof, "Stimulating Effect of Lactobacilli on the Growth of Propionibacteria in Cheese," *Neth. Milk Dairy J.* 23:287–289 (1969).

O'Leary et al., "Development of *B. Mesentericus* in Bread and Control with Calcium Acid Phosphate or Calcium Propionate," 18:730–740 (1941).

Olson et al., "Propionic Acid and Its Calcium and Sodium Salts as Inhibitors of Mold Growth," *J. Dairy Sci.* 23:509–510 (1940).

Reynolds et al., "Bactericidal Properties of Acetic and Propionic Acids on Pork Carcasses," *J. Animal Sci.* 38:515–519 (1974).

Skogen, "Capsulation of Propionibacterium," Iowa State University Master's Degree Thesis, pp. 69–71 (1970).

Suryarachchi et al., "Occurrence and Growth of Yeasts in Yogurts," *App. & Env. Microbiol.* 42:574–579 (1981).

Vedamuthu, "The Use of Candle Oats Jar Incubation for the Enumeration, Characterization and Taxonomic Study of Propionibacteria," *Milchwissenshaft* 22:428–431 (1967).

PROPIONIBACTERIA METABOLITES INHIBIT SPOILAGE YEAST IN FOODS

This is a continuation-in-part of Ser. No. 192,231, filed May 9, 1988, now U.S. Pat. No. 5,096,718, which is a continuation-in-part of Ser. No. 753,563, filed Jul. 10, 1985, now abandoned, which is a continuation-in-part of Ser. No. 419,559, filed Sep. 17, 1982, now abandoned.

SUMMARY OF THE INVENTION

The present invention relates to substances which inhibit yeast spoilage in food products.

The need for improved methods of food and feed preservation is great; activities of bacteria, molds, and yeasts render millions of pounds of food inedible annually and the problem is especially acute in countries with inadequate refrigeration. Among spoilage microorganisms, the yeasts are economically very significant because they are so versatile from nutritional and growth-temperature standpoints and because they are so ubiquitous. Yeasts are often the most difficult to inhibit of the food spoilage microorganisms.

Propionic acid is a known inhibitor of mold, but it is not useful to inhibit yeasts in foods. In bread, which is a high solids food, propionic acid or its salts are a preferred preservative in concentrations of 0.2% to 0.38% of the flour content to protect against mold because the propionic acid does not inhibit yeasts, which are necessary to make the bread rise. Propionic acid also finds use to inhibit only mold in stillage (Draughon et al., *J. Food Sci.* 47:1018, 1982), bread, and in certain food wrappers for use outside the food such as those for solid cheese (Ayres et al., *Microbiology of Foods*, W. H. Freeman and Co. 1980, p. 140; Moon, *Proc. Am. Soc. Microbiol.*, 1981, p. 29. Propionic acid is also identified specifically as an antimold agent in certain limited high solids foods such as Cold-Pack Cheese or Pasteurized Process Cheese, so long as these products contain no more than 0.3% by weight of sodium propionate, calcium propionate, or a combination of the two (21 CFR §133.123(6) and §133.169(7) [1991]). These cheeses have less than about 44% moisture (greater than 56% solids). The propionic acid can be produced chemically or by fermentation.

Propionibacteria are known to produce propionic acid and a relatively large amount of propionic acid is produced by a specific propionibacteria (*Propionibacterium acidipropionici* #B3568 — Anderson, U.S. Pat. No. 4,497,383). Propionic acid ($CH_3CH_2COOH$ — *The Merck Index*, 9th ed., Merck and Co., Inc., 1976) is known as a mold inhibitor, but is not known as a useful inhibitor of yeast in amounts which can be added to foods commonly spoiled by yeasts. Propionic acid has a distinct, unpleasant taste and stimulates the gag or vomiting reflex at concentrations lower than other similar organic acids such as acetic acid or citric acid.

If enough propionic acid is produced in a fermentation, then it has been shown that the fermented product can be used for its propionic acid content to inhibit mold in bread. Fermentation broth concentrations of propionic acid of >0.5% and preferably >1.3% are usually reached with the unique propionibacteria species *Propionibacterium acidipropionici* #B3568 (Anderson, U.S. Pat. No. 4,497,383). Mycostatic activity (mold inhibition) is reported to be directly proportional to the propionic acid produced in the fermentation process. A control fermentation of *P. shermanii* produced 0.80% propionic acid. *P. acidipropionici* was superior as a mycostatic agent by producing 0.96% propionic acid. Anderson suggests that if the fermented whey contains enough propionic acid, then it can be used for its propionic acid content as a mycostatic agent, and incorporated into breads, pastries and other bakery products to inhibit mold where yeast inhibition would interfere with making the bread product.

A report from Poland also shows that propionic acid produced by propionibacteria can be substituted for chemically produced propionic acid to inhibit mold in bread (Agric. Acad., Inst. Food Technol., Warsaw, Pol., *Zesz. Nauk. Szh. Gl. Gospod. Weijsk. Ikad, Roln, Warszagie, Technol. Riono-Spozyw.*, 12, pp. 23-26, 1977 [pubs. 1978]). After fermenting whey with *Propionibacterium petersonii* T-112 and incorporation to make bread, they found the flour contained 0.85% propionic acid and 0.34% acetic acid, and mold appearance was inhibited. They state that the bread contains at least twice the amount of propionic acid recognized to inhibit mold and suggest "future studies should involve lesser amounts of propionate (0.2% of the flour)." The findings of Anderson and the Polish article are not surprising since propionibacteria are known to produce >0.5% propionic acid, and concentrations of about 0.3% are used to inhibit mold.

Wolford et al. show that propionic acid can inhibit yeasts in high concentrations in nutrient broth ("Propionates Control Microbial Growth in Fruits, Vegetables", *Food Industries*, 17:622-625, 726, 728, 730, 732, 734 [June 1945]). They reported concentrations of 2.0% propionic acid were needed to inhibit one yeast and concentrations of 3.0% were needed to inhibit another yeast at pH 4.5, and higher amounts were needed at higher pH. These concentrations are much too high for use in food. Concentrations of propionic acid which are acceptable in bread or as approved in the Code of Federal Regulations for some cheese (~0.3% or less) were not effective against yeast.

An authoritative text (*Handbook of Food Additives*, 2nd ed., CRC Press, 1972, pp. 137-141) references the work of Wolford et al. and other long known appropriate literature on propionic acid, sodium propionate and calcium propionate and concluded that "propionates are more active against molds than sodium benzoate, but have essentially no activity against yeasts. They have little action against bacteria with notable exception of their ability to inhibit the organisms which cause rope." It is also reported that propionates "are suitable for yeast-raised as well as other baked goods" and "because propionates inhibit molds and spares yeast" they are used in breads (the *Handbook of Food Additives*, 2nd ed., CRC Press, 1972, pp. 137-141). A considerable body of literatures exists on propionibacteria which produce propionic acid. Their metabolites are not known to inhibit yeasts. Anderson (U.S. Pat. No. 4,497,833) teaches that the propionibacteria metabolites which contain enough propionic acid to inhibit mold can be used in yeast raised bread production.

Early literature (Shaw and Sherman, *J. Dairy Sci.* 6:303, 1923) reported that propionibacteria produce acetic and propionic acids. The production of other volatiles, namely acetaldehyde, propionaldehyde, ethanol, propanol and dimethyl sulfide, by these bacteria was noted by Keenan and Billis (*J. Dairy Sci.* 51:797, 1968). Diacetyl production by propionibacteria was reported by Lee et al. (*Can. J. Microbiol.* 16:1231, 1970). The *Handbook of Food Additives*, 2nd ed., (CRC Press, 1972) pp. 137-141, provides background information on propionic acid and its salts, including uses, physical and chemical properties, antimicrobial activity, safety, regulatory status, applications, handling, storage and assay. The same type of information on acetic acid and acetates is presented in this reference on pages 147-150. Propionibacteria are known to also produce succinic acid as well as acetic acid (Wood and Wekman, "Mechanism of Glucose Dissimilation by the Propionic Acid Bacteria," *Biochem. J.* 30:618-623, 1936; Wood and Wekman, "The Relationship of Bacterial Utilization of $CO_2$ to Succinic Acid Formation", *Biochem. J.* 34:129-137 (1940); Leaver, Wood and Stjerholm, "The Fermentation of Three Carbon Substrates by *C. Propionicum* and *Propionibacterium*", *J. Bacteriol.* 70:521-530, 1955.

When the metabolites of propionibacteria which contain enough propionic acid to inhibit mold are used in bread and other baked goods for their propionic acid content, the unpleasant flavoring acids and volatiles produced by propionibacteria are mostly removed during baking (*Baking Science and Technology*, 3rd ed., Vol. I, pp 247-248, E. J. Pyler, ed., Sosland Publishing Co., Merriam, Kans., 1988). This reference states: "Finally, during baking, the pH is again increased as a result of the volatilization, and removal, of a great proportion of the organic acids." The offensive odors and flavors of propionibacteria metabolites would not be removed in nonbaked products, which is a very good reason to avoid the use of propionibacterial culture mixtures in delicately flavored foods. It is not anticipated that a nutrient growth medium containing propionibacteria or their metabolites could be used as a liquid suspension, or after concentrating or drying as an additive to unbaked foods or feeds without producing an undesirable change in flavor or odor.

Just as propionic acid is useful to inhibit mold in certain foods with certain physical and chemical characteristics, there are other foods wherein propionic acid has no use or value even as an inhibitor of mold. Wolford (in his Table I) shows that 0.5% or more sodium propionate is needed to inhibit mold in a low solids broth if the pH is 5.0 or higher. Wolford concludes that propionate should be used with due regard to its limitations, such as the pH of the product, its microbial flora, and the concentration of propionate likely to impart foreign flavor or odor to the food. He shows that apple slices exposed for a short time to 0.5% calcium propionate carried a propionic odor. Meade and Stringham (U.S. Pat. No. 2,465,905) indicate that propionibacteria metabolites which contain 0.3% propionic acid produce a distinctive flavor to animal feeds. The Merck Index describes propionic acid as a substance with a "slightly pungent, disagreeable, rancid odor".

Meade provides information about the amount of propionic acid which is needed to inhibit mold at pH 4.7. For mold inhibition with propionibacteria metabolites, "The propionate radical concentration needed is inversely proportional to the solids content of the product." 0.3% propionic acid is needed in a 55% solids content product to inhibit mold and 0.5% is needed in a 50% solids product to inhibit mold (col 3, lines 35-44). Thus, as the solids decrease even a small amount, substantially more and more propionic acid is needed to inhibit mold when the propionic acid is in propionibacteria metabolites. The products of Anderson and Meade would not even be used to inhibit mold, let alone yeast, in food products with less than 50% solids. While Anderson discloses that propionibacteria fermented whey is useful as a preservative against mold in bread and baked products, which are very high solids foods with relatively low water activity, there is no reason to use such a product in certain cases.

Thus, certain foods (low solids, high pH) are not appropriate candidates for use of propionic acid as a mold inhibitor. One such food, for example, is cottage cheese. Cottage cheese is about 25% solids, and the pH is above 5.0, usually pH 5.2. If propionic acid were added to inhibit mold, more than 0.5% would be needed, and that would be too much. Further, cottage cheese is often spoiled by bacteria or yeast, but mold growth does not occur except in late stages of already spoiled product. There is no reason to add propionic acid or its salts to cottage cheese. And, there is no reason to add the metabolites of propionibacteria for their propionic acid content to cottage cheese. Logic dictates that one would not use something for its propionic acid content in a place or food where propionic acid is not used.

A survey of the market place confirms the above. If propionates had ever been used in cottage cheese, it would be well known in the literature since it is required that the use of propionates be identified on the food product label. A manufacturer that failed to state the presence of propionates would be guilty of misbranding. The inventors have examined over 8,000 cartons of cottage cheese from all over the United States and several European countries over the last 8 years and have never found any which contain propionates. This is not surprising since propionic acid (propionates) is not known to be inhibitory to yeast (or mold) in cottage cheese because of its physical (low solids) and chemical (pH > 5.0) characteristics, and since the action of propionic acid (antimold) is not what is needed to prevent cottage cheese spoilage. Other specific foods where propionic acid is not used for one or more of the above reasons include: yogurt, milk, half and half, whipping cream, buttermilk, salad dressing, and sour cream (cream cheese is 78% water, sour cream is 66% water, half and half is 70% water, and yogurt is 80% water). Applicants have now unexpectedly discovered that metabolites of propionibacteria inhibit yeast spoilage in all the above foods, and does so while providing far less than 0.5% propionic acid.

It is now discovered, quite surprisingly, that a mature propionibacterium growth medium can provide inhibition of yeasts. This effect can occur without providing an undesirable flavor, odor, or appearance, even in "delicate" foods. The unexpected findings disclosed are especially dramatic in light of the breadth of activity and some of the low concentrations which provide yeast inhibition. An antiyeast food additive can be obtained by growing propionibacteria, e.g. *Propionibacterium shermanii, P. freudenreichii, P. pentosaceum, P. thoenii, P. arabinosum, P. rubrum, P. jensenii, P. peterssonii,* and related species (as identified in Malik et al., *Can. J. Microbiol.* 14:1185, 1968) in a milk, cheese whey, or broth medium, or other suitable nutrient mixtures. The resulting growth liquid is then added to food and feed products other than bread or baked products to inhibit yeasts. To facilitate storage and shipment, the growth liquid may be dried to form a powder or frozen before use as an antiyeast food additive. The metabolites may be separated or purified or used as a mixture. Powdered or liquid natural metabolites of propionibacteria can be incorporated into various foods and feeds to render them less susceptible to spoilage by growth and/or enzymatic activity of yeasts. Antiyeast activity may be obtained by incorporating viable propionibacteria directly into a food.

The growth medium for such Propionibacterium species may be formulated with milk or whey containing yeast extractives or fruit juices or any other broth media containing appropriate growth nutrients. The growth liquid, after development of the propionibacteria up to $10^6$ to $10^{10}$ cells per ml, may be heat treated (pasteurized) to kill the inoculated and adventitious bacteria prior to use in liquid, condensed, dried, or frozen form. It is added in various concentrations (preferred between 0.01 and 10% of total weight) to food or feed where it functions to inhibit yeasts. This inhibition enables the shelf life and storage times of the food or feed to be increased.

These findings are surprising and have not previously been taught, because they have not been known. It is reported that neither propionic acid nor the metabolites of propionibacteria inhibit yeast to any useful amount when the propionic acid is less than 0.5% (Anderson, Wolford, and CRC Handbook). It is a general object of the present invention to extend the shelf life of food products subject to yeast spoilage by using the metabolites of propionibacteria to inhibit the spoilage yeast in a the food product which occurs under conditions where it has been reported that yeast are not inhibited.

Aspects of this invention have been discussed in U.S. patent application Ser. No. 192,231, filed May 9, 1988, which is a continuation-in-part of application Ser. No. 753,563, filed Jul. 10, 1985, now abandoned, which is a continuation-in-part of application Ser. No. 419,559, filed Sep. 17, 1982, now abandoned. Each of these prior applications is incorporated herein by reference.

An important object is to provide a substance which can be added to a food product to inhibit the growth of yeast without harming the flavor, aroma, or other characteristics of the food product.

A specific object is to extend the shelf life of dairy foods, cultured foods, and specifically cottage cheese, yogurt, Kissle-type products, fruit juice, salad dressings, pasta, sausages, and other meat products such as chicken, fish, crab, hamburger or others. In some cases the propionibacteria metabolites may be incorporated into a liquid or dressing which is applied to the food to provide the extension of shelf life.

An additional object is to provide a method which uses naturally produced substances in the preservation of food and feed.

A related object is to provide such a method which uses only a small quantity of such naturally produced substances.

It is also an object to provide antimicrobial substances which can be maintained in a dried or frozen form for simplicity of storage and shipment.

In certain embodiments, it is an object to provide an antiyeast food additive substance comprising a growth mixture containing bacteria and metabolites thereof, with the bacteria being viable or made not viable depending upon whether it is desired to produce additional amounts of metabolites after the antimicrobial substance is added to the food product.

These and other objects will become increasingly apparent by reference to the following description.

DETAILED DESCRIPTION

For the purpose of this disclosure, "metabolite" is defined as a substance, other than water, produced by propionibacteria. An "active metabolite" or an "inhibitory metabolite" is a metabolite which inhibits the growth or reproduction of an undesired yeast.

There are several aspects to the present invention as set forth below. It has been found possible to inhibit spoilage yeasts and thereby extend the shelf life of many food products without adversely affecting flavor or aroma by adding a growth mixture containing a propionibacterium culture with its metabolites or a fraction of such a growth mixture which fraction contains one or more inhibitory metabolites other than propionic acid. The mixture or fraction has a greater inhibitory effect than a weight of pure propionic acid which is equal to the pure propionic acid content of the mixture or fraction. Such substances are surprisingly excellent inhibitors of yeasts.

Examples of the present invention are set forth hereinafter. It is intended that they be only illustrative. Propionibacterium strains identified by number are available from the American Type Culture Collection (ATCC). The other cultures are widely available or can be obtained from Oregon State University, Corvallis, Oreg., without cost.

MIXED METABOLITES OF PROPIONIBACTERIA

It is discovered that Propionibacterium cultures can be used to produce a preservative material, including one or more metabolites (other than acetic acid, succinic acid and propionic acid) that inhibit yeast. A food product is preserved by providing in or on the product one or more of such active metabolites. The degree of inhibition achieved is much greater than is due to propionic acid in the mixtures of metabolites studied. In some cases where excellent inhibition occurs, the amount of propionic acid is so low as to have no measurable effect at all. And, propionic acid is known to not be a useful inhibitor of yeasts. This indicates that some other unidentified inhibitory substance or substances in propionibacteria growth mixtures is responsible for the excellent ability of such growth mixtures to extend the shelf life of food products against yeast spoilage.

Small amounts of viable propionibacteria are used in the manufacture of Swiss cheese to form eyes by the production of $CO_2$ and to impart the characteristic Swiss cheese flavor. In most food products, however, the presence of viable propionibacterial and Swiss cheese flavor would be unacceptable, eyes would not be desired, and $CO_2$ release may bloat packaging materials. Thus, as described in certain of the following examples, propionibacteria can also be grown in a liquid growth medium which is subsequently heated or otherwise treated to render the bacteria not viable. The result is a stable material which is an effective additive for the inhibition of spoilage yeast in food products.

To facilitate storage and shipping, a propionibacteria growth mixture may be frozen or concentrated, e.g., by spray-drying, or freeze-drying, to form a powder.

A preservative material according to the present invention is most readily used by mixing with a blendable food product, but should also be effective to treat the surface of solid food products, or the interior of such products, e.g. by injection. The optimum amount to be used will depend on the composition of the particular food product to be treated, but can be determined by simple experimentation.

In most instances, substantial improvements in shelf life can be obtained by adding the preservative material in an amount sufficiently small that it will have no deleterious effect on the flavor or aroma of the food product. This is possible because the material includes at least one propionibacteria metabolite which is active in inhibiting yeast and does not impart a strong flavor such as that of propionic acid.

The examples illustrate, generally, the effectiveness of propionibacteria growth mixtures as preservative materials against spoilage yeast.

EXAMPLE 1

*Propionibacterium shermanii* (ATCC Strain 9617 was grown in a sodium lactate broth for 48 hours. Five hundred gallons of skim milk were then pasteurized at 190° F. for 45 minutes, and subsequently cooled to 86° F. The cooled milk was acidified using 85% reagent grade lactic acid to a pH of 5.3 and then inoculated with 0.5% of the *Propionibacterium shermanii* culture. The inoculated milk was slowly agitated during incubation for 48 hours, and thereafter neutralized with sodium hydroxide to pH 7.0. The neutralized liquid was pasteurized at 145° F. for 20 minutes, cooled to ambient temperature (about 75° F.), pumped through sterile lines into six gallon sterile plastic bags and then frozen. Evidence that propionibacteria metabolites inhibit yeast and that there is a propionibacterial metabolite responsible for yeast inhibition which is not propionic acid is shown by the data below (Table 1) demonstrating that no correlation exists between propionic acid concentrations and yeast inhibition. Two different lots of inhibitor prepared as described above were found to have significantly different propionic acid concentrations. However each were shown to be equally effective in inhibiting yeast growth (assay procedure below). As a control, skim milk with added propionic acid was assayed for its inhibitory nature against yeast in an identical fashion. No inhibition was detected at any level of propionic acid tested, as expected based on literature teaching that propionic acid is not an effective inhibitor of yeast, and confirming that propionic acid is not the yeast inhibitor in propionibacteria metabolites. These data show a very new and unexpected use for propionibacteria metabolites which have previously not been recognized or used in this fashion. They show that propionibacteria produce at least one metabolite other than propionic acid, which has an inhibitory effect on a food spoilage yeast, and that a material containing the metabolite can be provided in a food product normally devoid of propionibacteria in an amount sufficient for the metabolite to inhibit the yeast. They also show that a propionic acid bacteria fermented material can comprise one or more metabolites other than propionic acid such that the material has a greater inhibitory effect than could be caused by its propionic acid content.

TABLE 1

PERCENT INHIBITION OF YEAST GROWN IN THE PRESENCE OF INHIBITOR
Control Colonies: 800 78 8

| | % Inhibitor* | % Inhibition | | | % Propionic Acid in Final Mixture |
|---|---|---|---|---|---|
| LOT NO. 023 | 1 | 25 | 50 | 100 | .0023 |
| | 5 | 75 | 100 | 100 | .0165 |
| | 10 | 100 | 100 | 100 | .0230 |
| LOT NO. 343 | 1 | 25 | 50 | 100 | .0002 |

TABLE 1-continued

| | | | | | |
|---|---|---|---|---|---|
| | 5 | 50 | 75 | 100 | .0010 |
| | 10 | 100 | 100 | 100 | .0020 |
| LOT NO. 023 | 2,270 ppm propionic acid (0.227%) | | | | |
| LOT NO. 343 | 243 ppm propionic acid (0.024%) | | | | |

PERCENT INHIBITION OF YEAST GROWN IN THE PRESENCE OF SKIM MILK PLUS PROPIONIC ACID
Control Colonies: 2000 187 25

| | % Additive** | % Inhibition | | | % Propionic Acid in Final Mixture |
|---|---|---|---|---|---|
| SKIM PLUS | 1 | 0 | 0 | 0 | .0023 |
| 243 ppm | 5 | 0 | 0 | 0 | .0165 |
| Propionic Acid | 10 | 0 | 0 | 0 | .0230 |
| SKIM PLUS | 1 | 0 | 0 | 0 | .0002 |
| 2270 ppm | 5 | 0 | 0 | 0 | .0010 |
| Propionic Acid | 0 | 0 | 0 | 0 | .002 |

*Percent of propionibacterial metabolites added to potato dextrose agar (PDA) containing yeast (see Yeast Assay which follows).
**Percent of additive (which was skim milk containing added propionic acid) added to potato dextrose agar (PDA) containing yeast.

These data show that a propionibacteria inhibitor product made according to the present invention can inhibit yeast even though it contains as little as 1/500th the amount of propionic acid that Wolford says is the minimum necessary to inhibit yeast. Different strains of propionibacteria may produce variable amounts of propionic acid and variable amounts of the newly discovered anti-yeast metabolites. Now that it is disclosed that propionibacteria can produce such anti-yeast metabolites, it is a simple matter for one skilled in the art to "screen" propionibacteria for their ability to produce inhibitors to yeasts. The present invention differs from any previous teachings as it is now revealed that there are previously unrecognized metabolites of propionibacteria which inhibit yeasts.

YEAST ASSAY AND INHIBITOR

The assay against yeast was conducted using potato dextrose agar (PDA), acidified to pH 4.0 and supplemented with INT to distinguish colonies from debris. Colonies on the plate will eventually "catch up" to the controls. As a result, the colonies are incubated at room temperature for two days, and then read. There should be a significant size difference (indicating fewer numbers of cells) between Inhibitor and control plates.

INT is p-Iodonitrotetrazolium Violet and is obtained from Sigma Chemical (Cat. #I-8377). It is prepared as a 0.29% solution in water and filter sterilized. Do not autoclave. INT is used at a level of 0.5 ml per 100 ml of melted and cooled agar. Colonies growing in the presence of INT will take on a red color.

EXAMPLE 2

Skim milk was fermented for four days with *Propionibacterium shermanii* (ATCC Strain 9616) with some agitation to prevent development of large cheese curds. The resulting metabolite mixture was neutralized to pH 6.0 with sodium hydroxide, screened and pasteurized with a HTST system. The resulting metabolite mixture had a concentration of propionic acid of 20,700 ppm, and acetic acid concentration of 13,100 ppm, as determined by gas chromatography.

Two vats of strawberry yogurt were made at a commercial dairy. Prior to pasteurization and setting, the acidified metabolite mixture was added to one vat at a concentration of 1.0%. Both vats of yogurt developed normally and the Propionibacterium metabolites did not inhibit the inoculation bacteria.

Samples taken from the two vats were plated at various times to monitor the growth of spoilage yeast present. Dilutions of each sample were plated with Potato-Dextrose agar (acidified with tartaric acid) using standard pour plate techniques. Plates were incubated for 3 days at 30° C., then counted. The results appear in Table II.

TABLE II

| | Yeast Counts | | |
|---|---|---|---|
| | 0 Day | 21 Days | 34 Days |
| Control | <10 | 23 | 900 |
| Metabolite Mix | <10 | 30 | 10 |

These results, in units of viable yeast per gram of yogurt, show control of spoilage yeast organisms which is not due to the final concentration of propionic acid added to the yogurt (which was only 0.02%). The yeast is inhibited by some metabolite of propionibacteria other than propionic acid. Thus, reference to propionic acid concentrations does not define the invention but only shows that other metabolites are active. This experiment shows the unexpected preservation of a food product against spoilage yeast comprising use of a propionibacteria fermented material. These data further show the use of a food preservative additive comprising a mixture of metabolites of propionibacteria which is more inhibitory to yeast than a weight of pure propionic acid which is equal to the pure propionic acid content of the mixture. The material produced by Propionibacterium contains a metabolite other than propionic acid which is present in an amount sufficient to inhibit the growth of yeast. This process can be applied to other dairy foods such as cottage cheese, milk, half and half, whipping cream, sour cream and salad dressings. The results are especially surprising since they show inhibiting spoilage yeast in a food product in circumstances where Wolford and Meade teach that yeast and even mold will not be inhibited. Both Wolford and Meade show that propionic acid in excess of the amount allowed in foods, where propionic acid has been used, would be required to inhibit yeast (or even mold), and the foods would carry the flavor or odor of propionic acid.

EXAMPLE 3

Metabolites of propionibacteria were prepared as described in Example 1. Commercially produced cottage cheese (150 cartons) was divided into 36 cartons of normally creamed controls and 114 cartons which were all creamed with standard dressing containing 1% of the propionibacteria metabolites. All samples were stored at 7° C. and sampled every 5 days for one month. Of the 36 control samples without propionibacteria metabolites, 12 were spoiled by yeasts ($5 \times 10^3$ to $4 \times 10^4$ cells/g) resulting in yeasty or sour off-flavors, and the other 24 samples were spoiled by gram negative bacteria ($10^7$ cells/g). Only 1 count of 114 (0.9%) samples of cottage cheese containing propionibacteria metabolites contained yeast. No adverse flavor effects were detected with the propionibacteria metabolites added to cottage cheese. This example is consistent with Example 2 in showing that propionibacteria metabolites inhibit yeast in cottage cheese. The metabolites of propionibacteria were mixed in the low solids liquid or dressing for the cottage cheese and added to the cheese curd. This example shows a process for inhibiting spoilage yeast in a food product, the process comprising combining a metabolite containing material produced by a Propionibacterium culture, the material being more inhibitory to yeast than a weight of propionic acid which is equal to the weight of propionic acid in the metabolite material, with a liquid or dressing product which contains less than 50% solids wherein the liquid or dressing product is to be combined with food solids to produce the food product, the material being present in the liquid or dressing product in an amount sufficient that the metabolite inhibits the yeast. The invention can also be used in a liquid or dressing of less than 50% solids to be applied to salads such as pasta or chicken or other meats or foods to inhibit yeast spoilage in the final food product.

EXAMPLE 4

Yogurt was prepared by inoculating 200 ml of 2% milk fortified with nonfat dry milk (4.5 g) and sugar (11.5 g) as a basal formula plus Propionibacterium metabolites as described below. Commercially available yogurt cultures (Hansen's) were used.

Propionibacterium (strain 9617) was grown for 96 hours in a mixture of whey (200 g), diammonium phosphate (12 g), and yeast extract (5 g), in 800 ml of water (identification symbol p-a) or in a formula of nonfat dry milk (200 g), diammonium phosphate (12 g), yeast extract (5 g), in 800 ml of water (identification p-b). Each of these growth media were then either freeze dried or heat dried. The following combinations of ingredients were then used to prepare yogurt. The basal media also initially contained sodium caseinate (1.0 g) unless specified otherwise below and in some cases a fruit flavor (10.0 g) was added after the yogurt had been formed. The following 12 formulae were tested.
1) Basal medium plus p-a (4.5 g) which had been freeze dried,
2) Basal medium plus p-a (4.5 g) which had been heat dried,
3) Basal medium plus p-a (4.5 g) which had been freeze dried and no flavor,
4) Basal medium plus p-a (4.5 g) which had been heat dried and no flavor,
5) Basal medium plus p-a (4.5 g) which had been heat dried and no sodium caseinate,
6) Basal medium plus p-a which had been heat dried, 4.5 g and no sodium caseinate and no flavor,
7) Basal medium plus p-b which had been freeze dried, 4.5 g,
8) Basal medium plus p-b which had been heat dried, 4.5 g,
9) Basal medium plus p-b which had been freeze dried, 4.5 g and no flavor,
10) Basal medium plus p-b which had been heat dried, 4.5 g and no flavor,
11) Basal medium plus p-b which had been heat dried, 4.5 g and no sodium caseinate,
12) Basal medium plus p-b which had been heat dried, 4.5 g and no sodium caseinate and non flavor.

Each of the above products produced an excellent yogurt with excellent viscosity and texture. There was no discernible inhibitory effect of the Propionibacterium metabolites on the bacteria which produced the yogurt. Those yogurts which had been prepared with p-b often had a solid or precipitate on the bottom which was readily dispersed and mixable with the products which contained flavor since the stirring of the flavor into the yogurt distributed any solid which had settled to the bottom. It is possible that the source of the solid was coagulated proteins which developed during the growth of Propionibacterium prior either to freeze drying or heat drying of the growth medium when nonfat dry milk was used as part of the nutrient medium, since a layer of solid or precipitated material did not develop in those formulae prepared with p-a which employed whey rather than nonfat dry milk.

The above products were prepared and stirred and three additional cups of yogurt which were purchased commercially were placed in identical containers and stirred and set out with these 12 products for a taste test by 3 individuals experienced in dairy microbiology and yogurt production. Combined, these individuals had 50 years experience in working with dairy products and have been involved in taste panels for judging yogurt. In general, the products prepared in this example were judged to be equal to the commercially-purchased products, and the preferred formulae were numbers 3, 4, 5, and 12 although the three "taste experts" did not agree on the order of superiority.

These products were kept in the refrigerator and examined daily. A commercially available flavored product exhibited large amounts of gas production and a yeasty odor and flavor 6 days after purchasing. An additional flavored yogurt which had been purchased also showed physical separation and had a very bad yeasty odor. There was no appearance of yeast in the formulas 1-12 above after 26 days. These results are consistent with Example 2 and demonstrate that the metabolite can be concentrated and freeze dried or heat dried and added as a concentrated material.

EXAMPLE 5

Yogurt Substitute Products

"Kissle" is a registered trademark for a commercially available, noncultured yogurt substitute. The product contains milk, cream, stabilizers, carbohydrates and protein. Chocolate, apricot, and blueberry flavored Kissle products were obtained commercially; and each was divided into controls and test samples.

The test samples were incorporated with 2¼% of powder produced by drying a Propionibacterium (ATCC Strain 9617) growth medium, and the products were then stored at either room or refrigeration (2°-5°C.) temperature. After 30 days, there was no yeast in any of the Kissle products which had the dried, powdered propionibacteria growth medium added at either room temperature or refrigeration temperature. The controls developed yeast gas bubbles at room temperature after three days. This example further indicates that the materials produced by growing propionibacterium can be effective at inhibiting yeast. The appearance, odor and flavor of these products with the extended shelf-life were all excellent.

EXAMPLE 6

Fruit Juice

The shelf life of a variety of fruit juices and related products was extended using propionibacteria according to the present invention.

Apple cider which had been filtered prior to packaging and another sample which had not been filtered, grape juice frozen concentrate, concentrated raspberry yogurt flavor and concentrated cherry yogurt flavor for use in yogurt were commercially obtained. Small paper cups were prepared containing about 100 g of each type of apple cider and of the concentrated grape juice and the grape juice after it had been diluted according to manufacturer's instructions, and the cherry yogurt flavor and of the raspberry yogurt flavor.

Five cups of each were prepared with one cup of each serving as a control. Other cups were inoculated with yeast and/or mold obtained from commercial yogurt. The second cup of each food product was inoculated with 1 ml of viable yeast cells only; and a third cup was inoculated with 1 ml of viable mold only. The fourth cup was inoculated with 1 ml of viable yeast and 3% of a heatdried powder produced from growing propionibacteria medium according to Example 5, and the fifth cup was inoculated with 1 ml of viable mold and 3% of the powdered propionibacteria growth medium. These were then stored at room temperature (uncovered). The following key was used to identify the effects:

1. Apple cider, filtered
   a. Mold
2. Unfiltered apple cider
   b. Yeast
3. Diluted grape juice
   c. Mold plus propionibacterium growth
4. Concentrated grape juice
   d. Yeast plus propionibacterium growth
5. Raspberry yogurt flavor
   e. Control On the second day, cup 1-b (apple cider filtered and inoculated with yeast) developed a yeasty odor and cup 3-b (diluted grape juice inoculated with yeast) also developed a yeasty odor. On the third day, cups 1-3 developed mold and cup 3-a also developed mold, and cup 4-b (concentrated grape juice inoculated with yeast) developed yeast. On the 4th day cup 1-a had mold, and cup 4-a had mold. However, cups c and d which were the products inoculated with mold and yeast and the powdered Propionibacterium growth medium did not have any mold or yeast even after four days at room temperature as contrasted to those samples which did not contain the Propionibacterium growth medium as described above.

This demonstrates a dramatic usefulness of the propionibacterium growth medium in inhibiting yeast in a variety of food products.

EXAMPLE 7

Two vats of sour cream were manufactured at a commercial dairy plant. Prior to pasteurization of the starting cream, one vat had a Propionibacterium metabolite mixture added at a level of 1.0%. The metabolite mixture had a concentration of propionic acid of 20,700 ppm, and acetic acid at a concentration of 13,100 ppm, as determined by gas chromatography prior to the addition which produced a propionic acid concentration of 0.02% in the sour cream.

After pasteurization, the cream was inoculated with gram positive starter organisms and incubated for 12 hours. The sour cream developed normally, and the starter culture bacteria were not inhibited by the Propionibacterium metabolite mixture. The sour cream was then packaged by machine in one pound cartons and cooled to 45° F. Cartons from the vat without the added metabolite mixture were used as controls.

To monitor the growth of spoilage yeast present, samples of control- and metabolite-containing sour cream were plated at various times. Dilutions of each sample were plated with potato-dextrose agar (acidified with tartaric acid) using standard pour plate technique.

Plates were incubated for 3 days at 30° C., then counted. The results, which appear in Table IV, show viable yeast cells per gram of sour cream have multiplied to much higher numbers in sour cream without the metabolite mixture.

Since propionic acid concentrations of 0.02% are not known to inhibit yeasts, this example shows that propionibacteria produce at least one metabolite other than propionic acid which has an inhibitory effect on yeast spoilage organisms, and the material can be provided in a cultured food product in an amount sufficient to inhibit the spoilage yeast, and the metabolites can be added prior to culturing. These data further show the preservation of a food product with a propionibacteria fermented medium that contains insufficient propionic acid to preserve the food product. More specifically, in a food product with less than 50% solids, Propionibacteria metabolites were inhibitory to yeast while not only providing much less than 1–3% propionic acid, but even while providing less than the 0.3% propionic acid which is allowed in some specific foods.

TABLE VI

| | YEAST RESULTS | | | | |
|---|---|---|---|---|---|
| | 0 Day | 7 Day | 14 Day | 21 Day | 33 Day |
| Control | 60 | 1,080 | 21,800 | 78,000 | 109,000 |
| Metabolite Mix | 90 | 100 | 500 | — | 24,200 |

EXAMPLE 8

Six different strains of propionibacterium were grown in a commercially available (Phase 4, Galloway-West Co., Fond Du Lac, Wis.) whey-based bulk starter medium. Six containers were prepared by adding 39 g of the medium to 500 ml of water, pasteurizing at 85° C. for 45 minutes, and cooling to 30° C. Each was then inoculated with 10 ml of one of 6 different cultures grown in tomato juice media for 24 hours. The propionibacterium cultures tested were: p-31-c; 13673; 8262; 9615; 9616; 9617. These were all obtained from the American Type Culture Collection in Rockville, Md.

After times 0, 16, 18, 21, and 24 hours, 25 ml of the growth media were removed by pipette, mixed with 25 ml of double strength potato dextrose agar (39 g for 500 ml of water) and the mixtures was autoclaved. After the potato dextrose agar and sample were mixed the sample was brought down to pH 3.0 to 3.7 with hydrochloride acid and poured into plates. The plates were dried overnight and then yeast was streaked onto each plate the next day and the plates were incubated at 33° C. for 24 hours. Plates containing the zero hour propionibacteria growth medium showed a large amount of yeast growth. The samples collected at 16, 18, 21, and 24 hours all allowed the growth of yeast. For p-31-c, yeast was apparent after 20 hours. For 13673, 8262, 9615, 9616, and 9617, yeast was present after 24 hours. Samples of growth media containing 9617 were somewhat inhibitory to yeast in this experiment as indicated by less growth of yeast on plates containing samples of 9617.

Duplicates of the above plates were prepared after continuing to grow the propionibacteria from 24 up to 80 hours and utilizing samples collected at times 0, 16, 18, 21, 24, and 80 hours after beginning of growth. Each plate was streaked with 2 different kinds of yeast. The results for these duplicate samples showed that for strain p-31-c, 8262, or 13673, none of the samples prevented complete growth of yeast. For strain 9615 the 80 hour sample was inhibitory to yeast. For strain 9616, the 80 hour sample was slightly inhibitory to yeast. For strain 9617, the 24 hour and 80 hour samples were inhibitory to yeast. For strain 13673, after 100 hours of growth there was inhibition of yeast with a 5 ml sample.

These show that strains 9615, 9616, 13673, and 9617 which have been allowed to grow for sufficient time under the conditions described herein can inhibit growth of yeast and that strains 9616 and 9617 were most active in inhibiting yeast. Although the amount of propionic acid produced was not determined by analysis, Anderson (U.S. Pat. No. 4,497,833) suggests that probably less than 1% propionic acid was produced which would provide only 0.05% (for 1 ml to 20 ml dilution) propionic acid in the yeast growth medium. Based on Example 2, the metabolites could have produced 0.1% propionic acid in the yeast growth medium. Based on literature teachings, the amount of propionic acid produced cannot account for the great activity of metabolite mixtures, as mentioned in the examples. It is not known which of the propionibacteria metabolites and combinations of metabolites is most effective in the inhibition of yeast. This example shows that a variety of propionibacteria produce a metabolite which is inhibiting to yeast, and now that this invention is discovered, it is an easy matter for one skilled in the art to identify those strains of propionibacteria which are most effective at producing yeast inhibitors using the procedures described herein, or other standard processes.

While we have described and given examples of preferred embodiments of our inventions, it will be apparent to those skilled in the art that changes and modifications may be made without departing from our inventions in their broader aspects. We therefore intend the appended claims to cover all such changes and modifications as fall within the true spirit and scope of our invention.

We claim:

1. A process for preserving a food product against spoilage yeast, the process comprising providing in a food product, that is normally devoid of Propionibacterium and is subject to spoilage by yeast, a metabolite-containing material that is produced by a culture of Propionibacterium and that contains a metabolite other than propionic acid, the material being present in an amount sufficient that the metabolite inhibits the growth of a spoilage yeast.

2. A process for preserving a food product against spoilage yeast, the process comprising providing in a food product that is subject to spoilage by yeast, a metabolite-containing material that is produced by a culture of Propionibacterium and that contains a metabolite other than propionic acid, the material being present in an amount sufficient that the metabolite inhibits the growth of a spoilage yeast, and wherein the food product is yogurt, cottage cheese, fruit juice, vegetable juice, milk, half and half, whipping cream, sour cream, salad dressing, or Kissle yogurt substitute.

3. A process for preserving a food product against spoilage yeast, the process comprising the step of providing in a food product, that is normally devoid of Propionibacterium and is subject to spoilage by yeast, a metabolite-containing material that is produced by a culture of Propionibacterium and that contains metabolites other than propionic acid, the material being present in an amount sufficient that the metabolite inhibits the growth of the spoilage yeast and that the material provides less than 0.3% propionic acid in the food product.

4. A process for preserving a food product against spoilage yeast, the process comprising the step of providing in a food product, that (a) is normally devoid of Propionibacterium, (b) contains less than 50% solids, and (c) is subject to spoilage by yeast, a metabolite-containing material that is produced by a culture of Propionibacterium and that contains metabolites other than propionic acid, the material being present in an amount sufficient that the metabolite inhibits the growth of the spoilage yeast and that the material provides less than 0.3% propionic acid in the food product.

* * * * *